US010875982B2

(12) United States Patent
Nagl et al.

(10) Patent No.: US 10,875,982 B2
(45) Date of Patent: Dec. 29, 2020

(54) BCHPC HAVING A REDUCED BURNING RATE

(71) Applicant: United Initiators GmbH, Pullach (DE)

(72) Inventors: Iris Nagl, Munich (DE); Gudrun Dischl, Munich (DE); Dominik Hermann, Dachau (DE); Daniel Canella, Munich (DE); Martin Kunz, Dettenhausen (DE); Kevin Guigley, Hernando, MS (US)

(73) Assignee: United Initiators GmbH, Pullach (DE)

(*) Notice: Subject to any disclaimer, the term of this patent is extended or adjusted under 35 U.S.C. 154(b) by 23 days.

(21) Appl. No.: 15/776,931

(22) PCT Filed: Nov. 23, 2016

(86) PCT No.: PCT/EP2016/078520
§ 371 (c)(1),
(2) Date: May 17, 2018

(87) PCT Pub. No.: WO2017/089375
PCT Pub. Date: Jun. 1, 2017

(65) Prior Publication Data
US 2019/0248983 A1  Aug. 15, 2019

(30) Foreign Application Priority Data
Nov. 23, 2015 (DE) .................. 10 2015 223 051

(51) Int. Cl.
| | |
|---|---|
| C08K 5/14 | (2006.01) |
| C08K 3/22 | (2006.01) |
| C08K 5/01 | (2006.01) |
| C08K 5/12 | (2006.01) |
| C08K 5/10 | (2006.01) |
| C08J 3/22 | (2006.01) |
| C07C 407/00 | (2006.01) |
| C08K 5/109 | (2006.01) |
| C08L 67/02 | (2006.01) |

(52) U.S. Cl.
CPC ............ *C08K 5/14* (2013.01); *C07C 407/006* (2013.01); *C08J 3/223* (2013.01); *C08K 3/22* (2013.01); *C08K 5/01* (2013.01); *C08K 5/10* (2013.01); *C08K 5/109* (2013.01); *C08K 5/12* (2013.01); *C08K 2003/2227* (2013.01); *C08K 2201/014* (2013.01); *C08L 67/02* (2013.01)

(58) Field of Classification Search
None
See application file for complete search history.

(56) References Cited

U.S. PATENT DOCUMENTS

| | | | |
|---|---|---|---|
| 3,538,011 A * | 11/1970 | Van Der Klaauw | ....................... C07C 407/006 252/186.26 |
| 3,878,166 A | 4/1975 | Woycheshin et al. | |
| 4,039,475 A | 8/1977 | Oosterwijk et al. | |
| 5,314,639 A * | 5/1994 | Torenbeek | ............ C07C 409/22 252/186.21 |
| 5,347,055 A | 9/1994 | Priddy et al. | |
| 2008/0125504 A1 | 5/2008 | Reinheimer | |

FOREIGN PATENT DOCUMENTS

| | | |
|---|---|---|
| CA | 1136600 | 11/1982 |
| CN | 103865165 A | 6/2014 |
| DE | 10130772 C1 | 3/2003 |
| DE | 102011102682 A1 | 11/2012 |
| EP | 3034551 A1 | 6/2016 |
| JP | 2008-169154 A | 7/2008 |
| WO | 01/46309 A1 | 6/2001 |

OTHER PUBLICATIONS

PCT International Search Report and Written Opinion for PCT Application No. PCT/EP2016/078520 dated Feb. 10, 2017 (11 pages).
German Examination Report for DE Application No. 102015223051.1 dated Aug. 4, 2016 (8 pages).
Japanese Office Action for JP Application No. 2018-545689 dated Aug. 31, 2020 (7 pages).

* cited by examiner

*Primary Examiner* — Robert T Butcher
(74) *Attorney, Agent, or Firm* — Eversheds Sutherland (US) LLP

(57) ABSTRACT

The invention relates to the reduction of the burning rate of di-(4-tert-butylcyclohexyl)-peroxydicarbonate (BCHPC) by adding desensitizers as well as to the use of BCHPC preparations having a reduced burning rate as an initiator in chemical reactions.

20 Claims, 5 Drawing Sheets

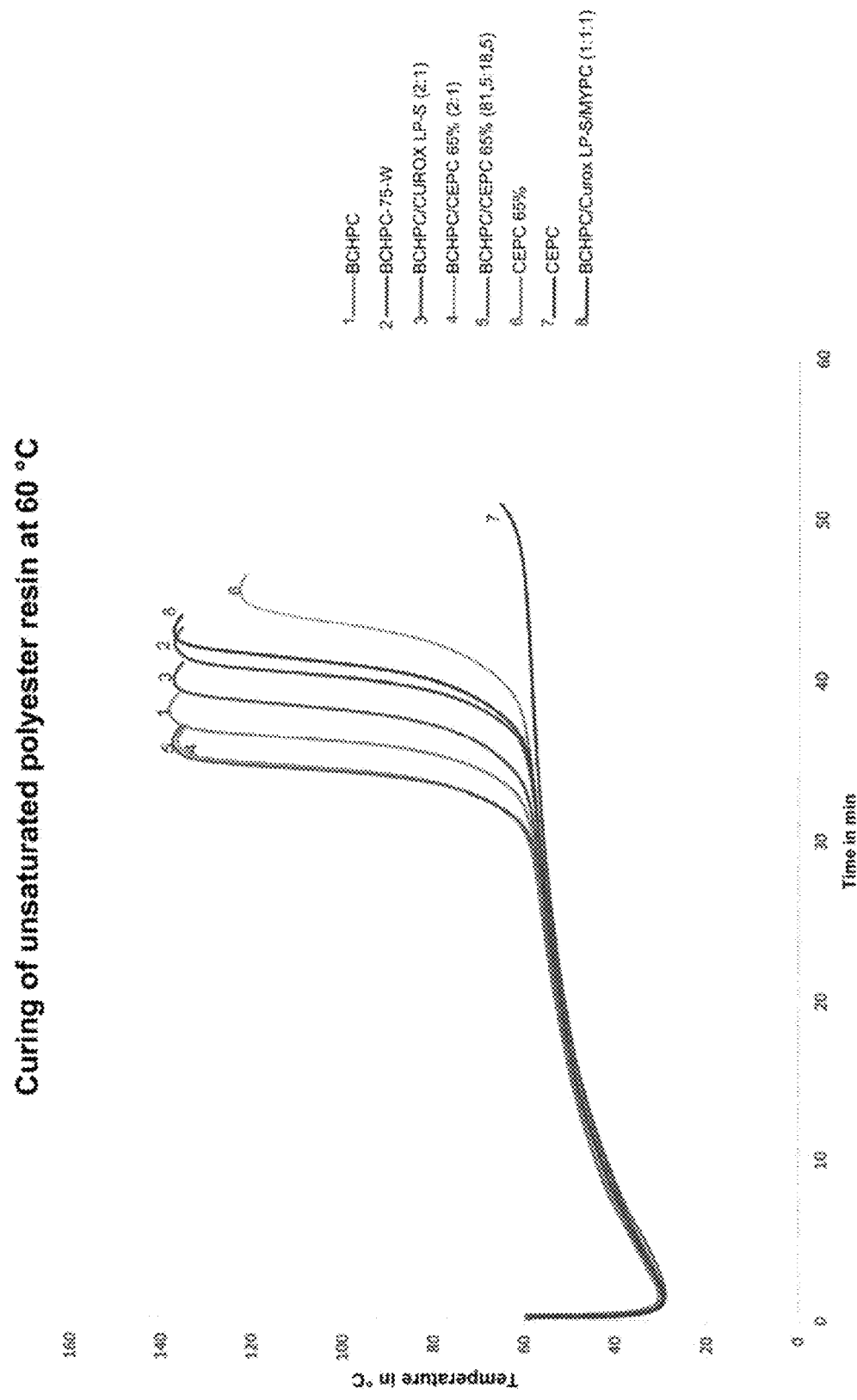

BCHPC HAVING A REDUCED BURNING RATE

CROSS REFERENCE TO RELATED APPLICATIONS

This application claims the priority benefit of PCT/EP2016/078520 filed on Nov. 23, 2016 which claims priority benefit of German Application No. 10 2015 223 051.1 filed Nov. 23, 2015. The entire contents of which are hereby incorporated by reference herein.

The present invention relates to the reduction of the burning rate of di-(4-tert-butylcyclohexyl)-peroxydicarbonate (BCHPC) by adding desensitising agents and to the use of BCHPC preparations having a reduced burning rate as an initiator in chemical reactions.

Di-(4-tert-butylcyclohexyl)-peroxydicarbonate (BCHPC) is a much-used, solid initiator for curing unsaturated polyester resins. The disadvantage of BCHPC is its relatively high burning rate, which results in this peroxide being classified in Hazard Class 1 a (Germany) or 1 (the Netherlands and United States) (in Germany according to BG regulation B4, § 3 and Annex 2, date: June 2013). High technical requirements are thus associated with safe storage.

The object of the present invention was therefore to reduce the burning rate of BCHPC and to provide a preparation of this peroxydicarbonate that has a reduced burning rate compared to pure BCHPC. Advantageously, the preparation should be as well suited as pure BCHPC as an initiator in a chemical reaction.

It is known from DE 1 618 726 and DE 10 2011 102 682 A1 [0003] that sensitivity to impact and friction and the explosive properties of organic peroxides can be improved if a preparation is produced having a solid desensitising agent. What was previously unknown was that the burning rate can also be reduced in this way.

In the present invention it has now been surprisingly found that the burning rate of BCHPC can be substantially reduced if BCHPC is mixed with certain substances, which are able to reduce the burning rate and to maintain the desired functionality of BCHPC as an initiator for chemical reactions. According to a first aspect of the invention, desensitising agents are used as substances suitable for reducing the rate of burning. In the context of the invention, the term "desensitising agent" denotes a solid that is inert towards BCHPC.

A first aspect of the present invention therefore relates to the use of at least one desensitising agent for reducing the burning rate of di-(4-tert-butylcyclohexyl)-peroxydicarbonate (BCHPC), comprising the provision of a mixture that comprises BCHPC and at least one desensitising agent.

In the context of the present invention, any desensitising agents known in the art, such as described in DE 1 6180726 and DE10 2011 102 682 A1, are, in principle, suitable as "desensitising agents". Particularly suitable are dicyclohexyl phthalate, fluorene, aluminium trihydroxide, polystyrene, CC initiators such as CUROX CC-DC and glyceryl tribenzoate, as well as combinations of two or more of these desensitising agents.

The desensitising agent is used in a preferred embodiment in such a quantity that the ratio of BCHPC to desensitising agent is 10:90 to 90:10 wt. %. 25:75 to 75:25 wt. % or 40:60 to 60:40 wt. % is preferred.

When using a desensitising agent for reducing the burning rate of BCHPC, preferably no further components are added to the mixture of BCHPC and desensitising agent. However, it is generally possible to combine the use of the desensitising agent with other additives. For example, a mixture of BCHPC and desensitising agent may further comprise polymers or fillers. Examples of suitable fillers are chalk, silica, silicates, phthalates, and/or benzoates.

In a preferred embodiment the proportion of BCHPC relative to the total mixture of BCHPC and desensitising agent as well as optionally further components is 10 to 90 wt. %, more preferably 25 to 75 wt. % or 30 to 60 wt. %.

For the use of one or more desensitising agents for reducing the burning rate of BCHPC, BCHPC and desensitising agents can, in principle, be combined in any manner. Suitable methods are described, for example, in DE 1 6180726 and DE10 2011 102 682.

In a preferred aspect of the invention, the use of one or more desensitising agents for reducing the burning rate of BCHPC comprises the following steps:

(i) mixing BCHPC with at least one desensitising agent, wherein BCHPC is present in solid form, in the form of a solution in an organic solvent or in the form of an aqueous suspension, and the at least one desensitising agent is present in solid form, as a melt or in the form of a solution or suspension in an organic or aqueous solvent, (ii) optional removal of solvent and/or water and (iii) optional drying.

BCHPC is preferably used in solid form, for example in powder form. Here BCHPC may be dry or moistened with water. The use of BCHPC as a dry powder is preferred. Alternatively BCHPC can also be used in the form of an aqueous suspension or a solution in an organic solvent.

The desensitising agent(s) is/are preferably likewise used in solid form, for example in powder form, dry or moistened with water. Alternatively, use in the form of a melt or in the form of a solution or suspension in an organic or aqueous solvent is also possible.

If BCHPC and/or desensitising agent are used in the form of a solution or suspension, solvent and/or water are removed in step (ii). Any process steps are suitable, in principle, for this purpose, such as filtration, for example. In the process, the BCHPC-desensitising agent mixture is separated from the liquid phase.

Finally, drying can optionally take place in step (iii). Alternatively, drying can also be dispensed with and the BCHPC-desensitising agent mixture can be provided in water-moistened form.

In a further embodiment of the invention, the use of desensitising agent for reducing the burning rate of BCHPC takes place during the manufacture of BCHPC. For this purpose, in step (i), at least one desensitising agent can be dissolved in a precursor of BCHPC or in an aqueous solution or suspension of the precursor of BCHPC. Butylcyclohexyl chloroformate, for example, can act as a precursor of BCHPC. The solution thus obtained is then reacted in step (ii) with a mixture of aqueous sodium peroxide and sodium hydroxide solution. The BCHPC/desensitising agent mixture is separated in step (iii), and finally dried, if desired, in step (iv).

The mixture resulting from the use of one or more desensitising agents for reducing the burning rate of BCHPC is present in solid form in a preferred embodiment of the invention, for example in powder form. In this case, the mixture can be provided dry or in a water-moistened form.

In the present invention it was also surprisingly found that the burning rate of BCHPC can also be reduced if at least one further organic peroxide is admixed.

A further aspect of the present invention therefore relates to the use of at least one organic peroxide for reducing the burning rate of BCHPC, comprising the provision of a mixture that comprises BCHPC and at least one further organic peroxide. It is particularly surprising here that the initiator activity of BCHPC is maintained and even improved in some cases.

Organic peroxides in particular, which are selected from dilauroyl peroxide (LP), dicetyl peroxydicarbonate (CEPC) and dimyristyl peroxydicarbonate (MYPC), are suitable according to the invention for use in reducing the burning rate of BCHPC. Mixtures of two or more of these peroxides are also suitable.

The suitability of organic peroxides for reducing the burning rate of BCHPC is particularly surprising, since further active oxygen is introduced into the preparation thereby. Nevertheless, it was found that the burning rate can be substantially reduced.

The at least one organic peroxide is used in a preferred embodiment in such a quantity that the ratio of BCHPC to organic peroxide is 10:90 to 90:10 wt. %. 25:75 to 75:25 wt. % or 40:60 to 60:40 wt. % are preferred.

When using one or more organic peroxides to reduce the burning rate of BCHPC, preferably no further components are added to the mixture of BCHPC and organic peroxide. However, it is generally possible to combine the use of organic peroxide with further additives. For example, a mixture of BCHPC and organic peroxide may further comprise polymers or fillers. Examples of suitable fillers are chalk, silica, silicates, phthalates, and/or benzoates.

In a preferred embodiment, the proportion of BCHPC relative to the total mixture of BCHPC and organic peroxide and optionally further components is 10 to 90 wt. %, more preferably 25 to 75 wt. % or 30 to 60 wt. %.

For the use of one or more organic peroxides for reducing the burning rate of BCHPC, BCHPC and organic peroxide can be combined with one another in principle in any manner. Suitable methods are described, for example, in DE 1 6180726 and DE10 2011 102 682.

In a particularly preferred embodiment of the present invention, the use of at least one organic peroxide for reducing the burning rate of BCHPC comprises the following steps:
(i) mixing BCHPC with at least one further organic peroxide, wherein BCHPC is present in solid form, in the form of a solution in an organic solvent or in the form of an aqueous suspension and
the at least one further organic peroxide is present in solid form, in the form of a solution in an organic solvent or in the form of an aqueous suspension,
(ii) optional removal of solvent and/or water and
(iii) optional drying.

BCHPC is preferably used in solid form or in the form of an aqueous suspension and mixed with one or more organic peroxides, which are also present in solid form or in the form of an aqueous suspension. BCHPC and organic peroxide are particularly preferably used in each case in solid, dry or water-moistened form and mixed with one another.

If the individual components are used in the form of a solution or suspension, step (ii) provides the removal of solvent and/or water. Here separation of the BCHPC/organic peroxide mixture takes place, for example by filtration.

If required, the mixture obtained may be dried in step (iii). Alternatively, the mixture may also be provided in water-moistened form.

In a preferred embodiment of the invention the mixture resulting from the use of one or more organic peroxides for reducing the burning rate of BCHPC is present in solid form, for example in powder form. In this case, the mixture can be provided in dry or water-moistened form.

In a further embodiment of the present invention, a combination of at least one organic peroxide and at least one desensitising agent is used for reducing the burning rate of BCHPC. Desensitising agents and organic peroxides are defined in this case as above.

When using a combination of organic peroxide and desensitising agent for reducing the burning rate of BCHPC, preferably no other components are added to the mixture of BCHPC, organic peroxide and desensitising agent. However, it is possible, in principle, to combine the use of organic peroxide and desensitising agent with other additives. For example, a BCHPC/organic peroxide/desensitising agent mixture may further comprise polymers or fillers. Examples of suitable fillers are chalk, silica, silicates, phthalates, and/or benzoates.

The total quantity of organic peroxide and desensitising agent is preferably selected such that the proportion of BCHPC relative to the total mixture is 10 to 90 wt. %, preferably 25 to 75 wt. % or 30 to 60 wt. %. The mixture preferably contains no additional components apart from BCHPC, organic peroxide and desensitising agent.

In the combination of organic peroxide and desensitising agent for reducing the burning rate of BCHPC, the quantity of organic peroxide is preferably selected such that the ratio of BCHPC to further organic peroxide is 10:90 to 90:10 wt. %, preferably 25:75 to 75:25 wt. % or 40:60 to 60:40 wt. %. The quantity of desensitising agent is preferably selected such that the ratio of BCHPC to desensitising agent is 10:90 to 90:10 wt. %, preferably 25:75 to 75:25 wt. % or 40:60 to 60:40 wt. %.

For the use of one or more desensitising agents in combination with one or more organic peroxides for reducing the burning rate of BCHPC, the individual components can, in principle, be combined with one another in any manner. Organic peroxide and desensitising agent can be mixed simultaneously or successively with BCHPC. Suitable methods are, for example, the methods described in DE 1 618 726 and DE10 2011 102 682 for the combination of peroxide and desensitising agent.

In a preferred embodiment, the use of a combination of organic peroxide and desensitising agent for reducing the burning rate of BCHPC comprises the following steps:
(i) mixing BCHPC with the at least one organic peroxide and the at least one desensitising agent,
wherein BCHPC is present in solid form, in the form of a solution in an organic solvent or in the form of an aqueous suspension,
the at least one further organic peroxide is present in solid form, in the form of a solution in an organic solvent or in the form of an aqueous suspension and
the at least one desensitising agent is present in solid form, in the form of a solution or suspension in an organic or aqueous solvent,
(ii) optional removal of solvent and/or water and
(iii) optional drying.

BCHPC, desensitising agent and organic peroxide are preferably mixed with one another in each case in solid form or in the form of an aqueous suspension or solution. Particularly preferably, all of the components are present in solid form, for example in powder form, dry or moistened with water.

If one or more components are used in the form of a solution or suspension, separation of the BCHPC/organic peroxide/desensitising agent mixture from solvent and/or water takes place in step (ii). Filtration, for example, is suitable for this.

Finally, the mixture obtained may be dried in step (iii). Alternatively, the mixture may also be provided in water-moistened form.

In a preferred embodiment of the invention the mixture resulting from the use of a combination of organic peroxide and desensitising agent for reducing the burning rate of BCHPC is present in solid form, for example in powder form. In this case, the mixture can be provided dry or in water-moistened form.

Another aspect of the invention relates to a composition comprising BCHPC and at least one substance for reducing the rate of burning. The substance relating to the reduction in the burning rate is selected from organic peroxides, desensitising agents and mixtures thereof as defined above.

The composition preferably contains no further constituents in addition to BCHPC, organic peroxide and desensitising agent. However, it is, in principle, possible to add other substances too, such as in particular polymers or fillers. Examples of suitable fillers are chalk, silica, silicates, phthalates, and/or benzoates.

In a preferred embodiment, the composition is present in solid form, for example in powder form. The composition can be present in dry or water-moistened form.

The quantity ratio of BCHPC, organic peroxide and desensitising agent can be adjusted as desired. For example, the proportion of BCHPC relative to the composition can be 10 to 90 wt. %, preferably 25 to 75 wt. % or 30 to 60 wt. %. In a preferred embodiment, the composition contains no further constituents in addition to BCHPC, organic peroxide and desensitising agent.

In the composition according to the invention, the ratio of BCHPC to further organic peroxide is preferably 10:90 to 90:10 wt. %, more preferably 25:75 to 75:25 wt. %, or 40:60 to 60:40 wt. %. The ratio of BCHPC to desensitising agent may, for example, be 10:90 to 90:10 wt. %, preferably 25:75 to 75:25 wt. % or 40:60 to 60:40 wt. %.

A composition according to the invention can be used, for example, as an initiator in a chemical reaction. The composition is particularly suitable for use in a method for curing, for example of an unsaturated polyester resin.

When used as an initiator for a method for curing, in particular the use of one or more organic peroxides for reducing the burning rate of BCHPC proves particularly favourable. In this case, it is possible to almost maintain the cure rate compared to undiluted BCHPC. Although the mixture exhibits a substantially lower rate of burning, the cure rate remains substantially unaffected when used as an initiator for the curing of an unsaturated polyester resin. The use of dicetyl peroxydicarbonate (CEPC) has proved particularly suitable in this context. Here it was surprisingly found that the cure rate even increases compared to undiluted BCHPC.

The invention will be illustrated further by the following figures and examples.

FIG. 1: Burning rate of BCHPC compared to different BCHPC preparations having desensitising agents. Preparations of BCHPC having CUROX LP-S, glyceryl tribenzoate, CUROX CC-DC, aluminium trihydroxide, polystyrene, dicyclohexyl phthalate, or fluorene are shown.

FIG. 2: Burning rate of BCHPC having dicyclohexyl phthalate in different mixing ratios.

FIG. 3: Burning rates of BCHPC preparations having various organic peroxides.

FIG. 4: Temperature profile during the curing having various BCHPC preparations. Shown are the results for dry BCHPC (BCHPC), water-moistened BCHPC (BCHPC-75-W), dry CEPC (CEPC), water-moistened CEPC 65%, and for combinations of dry BCHPC with CUROX LP-S, CEPC 65% or CUROX LP-S and MYPC.

EXAMPLES

1. Analysis of the Burning Rate
1.1 Combination of BCHPC with Different Desensitising Agents Various mixtures of BCHPC were produced having different desensitising agents and analysed with regard to their burning rates.

The following combinations of BCHPC with peroxide or desensitising agents were analysed:
BCHPC: CUROX LP-S(2:1)
BCHPC: Glyceryl tribenzoate (2:1)
BCHPC: CUROX CC-DC (2:1)
BCHPC: Aluminium trihydroxide (2:1)
BCHPC: Polystyrene (2:1)
BCHPC: Dicyclohexyl phthalate (2:1)
BCHPC: Fluorene (2:1)
BCHPC The indications of the quantity ratios describe weight ratios in each case.

CUROX LP-S is a 75 to 80%, water-moistened dilauroyl peroxide from United Initiators GmbH & Co. KG.

CUROX CC-DC (or CCDFB-90) is a non-peroxidic CC initiator from United Initiators GmbH & Co. KG, 2,3-Dimethyl-2,3-diphenylbutane.

Figure 1:
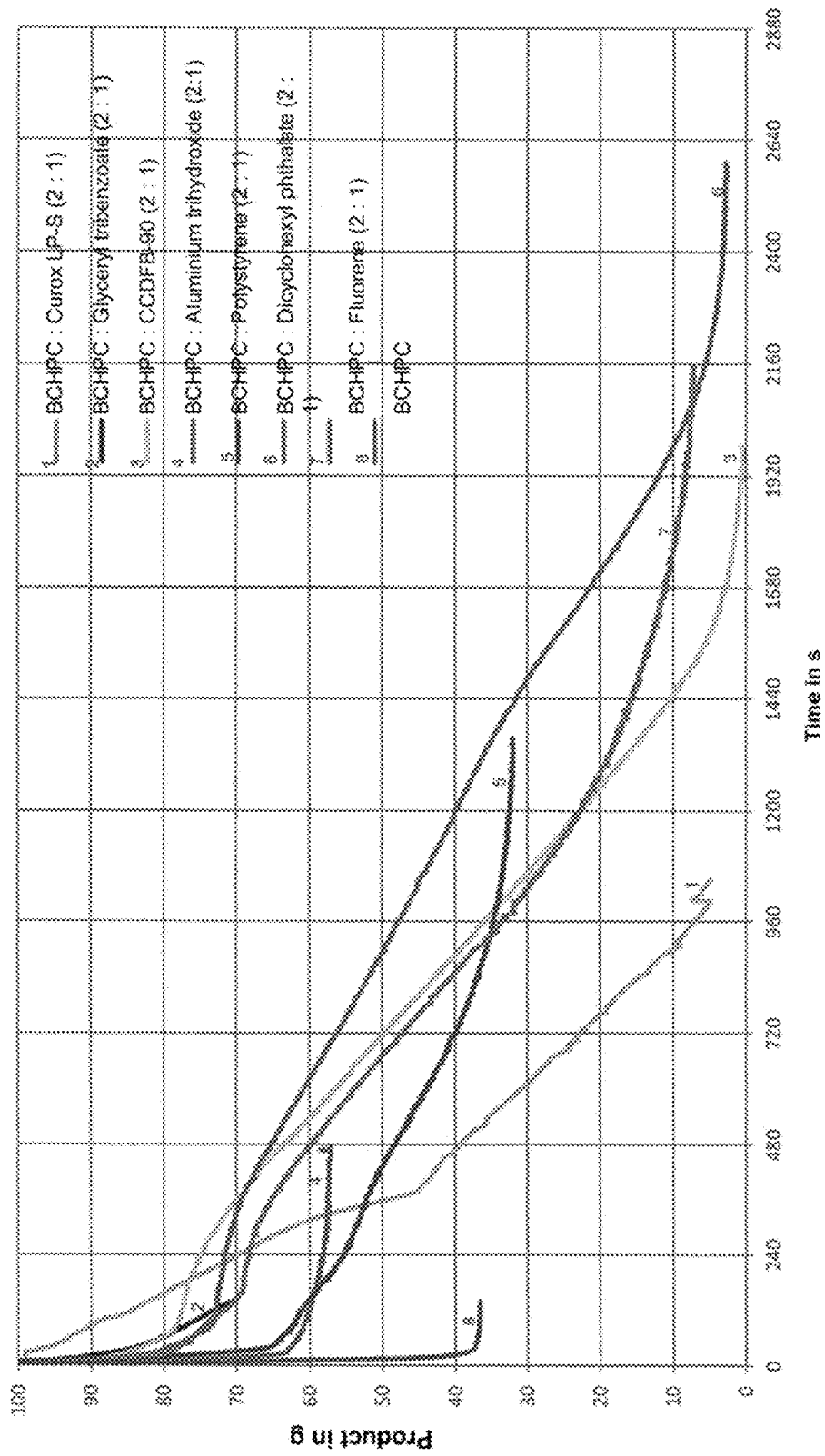

In order to be able to compare the burning rates of the various mixtures, 100 g of the preparation were ignited in each case and the amount of the substance still remaining was determined with respect to time. The procedure corresponds to BG regulation B4, Annex 4, version dated 1 Jan. 1997, Annex 4 for liquids. The procedure was adapted to solids. The results are shown in FIG. 1.

It was found that the burning rate decreases when BCHPC powder is mixed with an inert solid such as dicyclohexyl phthalate, fluorene, aluminium trihydroxide, polystyrene and glyceryl tribenzoate.

1.2 Combination of BCHPC with Dicylohexyl Phthalate in Different Mixing Ratios

Figure 2:
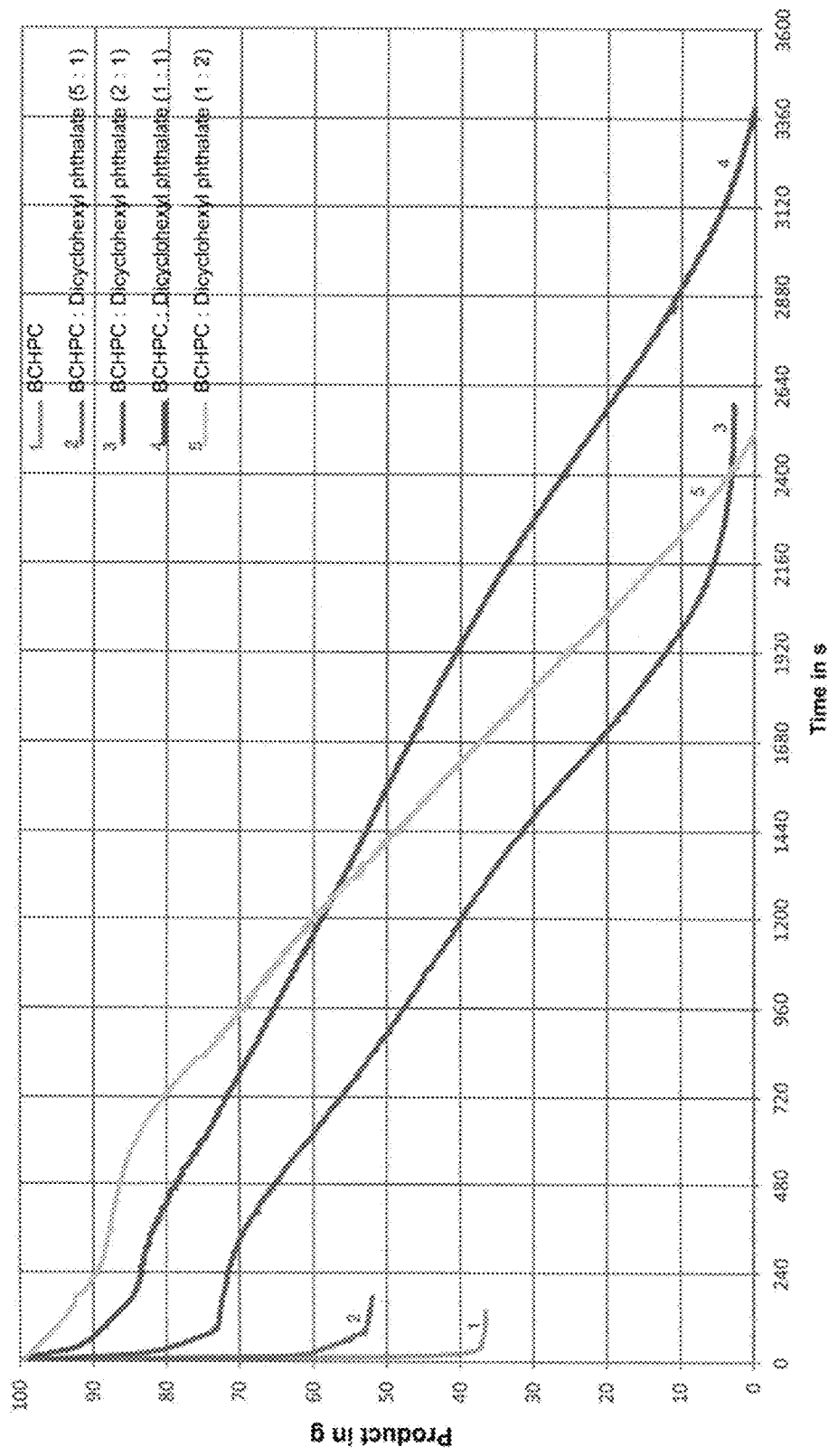

To analyse the influence of the quantity of desensitising agent used on the burning rate, combinations of BCHPC with dicyclohexyl phthalate in different mixing ratios were produced. The burning rate was analysed as described in Example 1.1. The mixtures tested were BCHPC: dicyclohexyl phthalate in a ratio of 5:1, 2:1 and 1:1 as well as pure BCHPC. It was found that with the addition of a larger quantity of desensitising agent, the burning rate also decreases further. The results are shown in FIG. 2.

1.3 Combination of BCHPC with Organic Peroxide

Figure 3A:
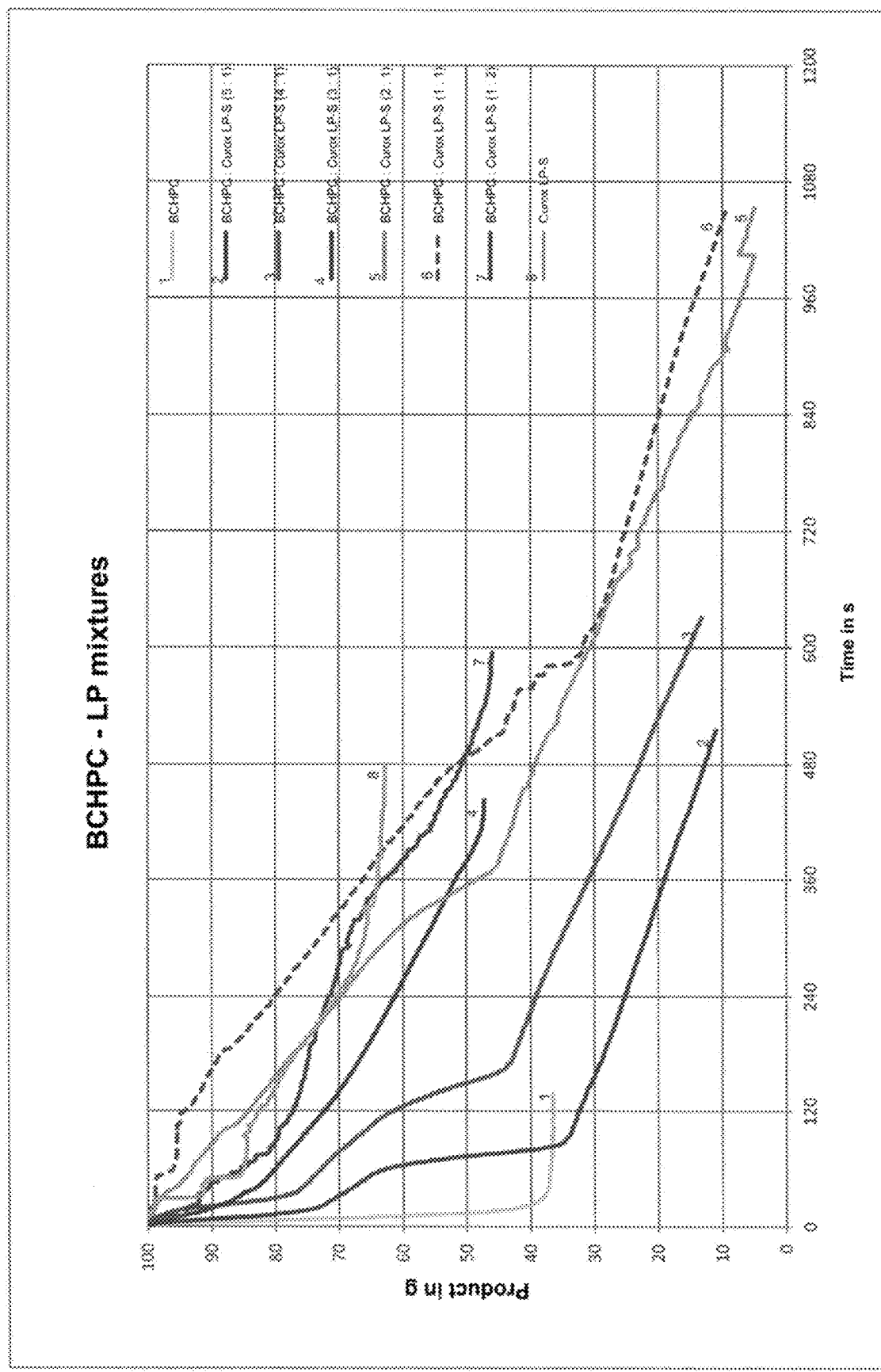
FIG. 3A shows preparations of BCHPC having CUROX LP-S in various mixing ratios in comparison with pure CUROX LP-S and BCHPC.
Figure 3B:
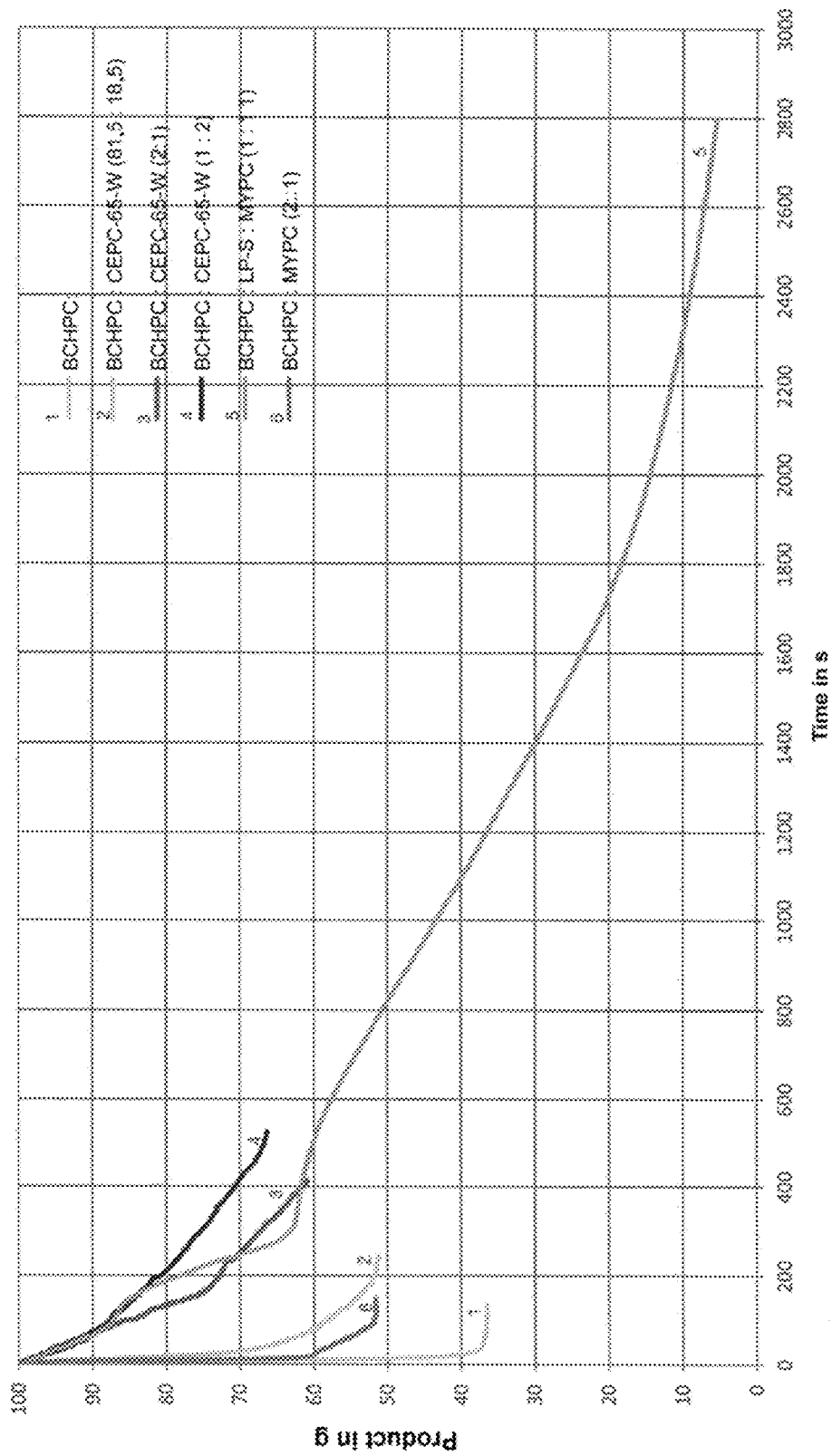
FIG. 3B shows the results for mixtures of BCHPC with CEPC 65% in various mixing ratios, and for mixtures of BCHPC with MYPC or with a combination of CUROX LP-S and MYPC, compared to pure BCHPC.

To analyse the rate of burning of a mixture of BCHPC with one or more further organic peroxides, combinations of BCHPC with dilauroyl peroxide (LP) or dicetyl peroxydicarbonate (CEPC) were produced in various mixing ratios. In addition, combinations of BCHPC with dilauroyl peroxide and myristyl peroxydicarbonate (MYPC) in the ratio 1:1:1 or BCHPC with MYPC in the ratio 2:1 were examined. The analysis of the rate of burning was carried out as described in Example 1.1. The results are shown in FIGS. 3A and 3B.

For mixtures of BCHPC and LP, comparisons of mixing ratios of 5:1, 4:1, 3:1, 2:1, 1:1 and 1:2 were examined. The burning rate was lower in each case than observed for pure BCHPC. In the case of an excess of dilauroyl peroxide (BCHP: CUROX LP-S=1:2) the rate of burning is not so significantly reduced as in a ratio of 1:1, but the ignition of the mixture took significantly longer than with the other mixtures.

For combinations of BCHPC with dicetyl peroxydicarbonate, the mixing ratios 81.5:18.5, 2:1 and 1:2 were analysed.

It can be seen that in all cases the combustion of the mixtures compared to pure BCHPC is significantly delayed, although the BCHPC is combined with one or more further organic peroxides, due to which, further active oxygen is introduced into the preparation.

2. Cure Rate of Various BCHPC Preparations

To analyse the cure rate of mixtures of BCHPC and various organic peroxides, a curing test was conducted in accordance with DIN16945. The following mixtures were analysed:
BCHPC
BCHPC-75-W
BCHPC/CUROX LP-S(80%)-2:1
BCHPC/CEPC 65%-2:1
BCHPC/CEPC 65% (81.5:18.5)
CEPC 65%
CEPC
BCHPC/CUROX LP-S/MYPC (1:1:1)

CEPC 65% is an approximately 65% water-moistened dicetyl peroxydicarbonate. It was found that with the various mixtures analysed, the cure rate compared with undiluted BCHPC decreases only slightly. In the case of the mixture of BCHPC and water-moistened CEPC powder, even an increase in the curing rate was observed. The results are shown in FIG. 4.

The invention claimed is:

1. A use of at least one organic peroxide for reducing the burning rate of di-(4-tert-butylcyclohexyl)-peroxydicarbonate (BCHPC), comprising providing a mixture that comprises BCHPC and at least one further organic peroxide and at least one desensitising agent, wherein the at least one desensitising agent is an inert solid towards BCHPC,
wherein the proportion of BCHPC relative to the mixture of BCHPC and further organic peroxide and desensitising agent is 10 to 90 wt. %, and
wherein the ratio of BCHPC to further organic peroxide is 25:75 wt. % to 75:25 wt. %.

2. The use according to claim 1, wherein the mixture is present in solid form.

3. The use according to claim 1, wherein at least one organic peroxide is used, which is selected from dilauroyl peroxide (LP), dicetyl peroxydicarbonate (CEPC) and dimyristyl peroxydicarbonate (MYPC).

4. The use according to claim 1, wherein at least one desensitising agent is used, which is selected from dicyclohexyl phthalate, fluorene, aluminium trihydroxide, polystyrene and glyceryl tribenzoate.

5. The use according to claim 1, wherein the ratio of BCHPC to further organic peroxide is 25 to 75 wt. %.

6. The use according to claim 1, wherein the ratio of BCHPC to desensitising agent is 10:90 wt. % to 90:10 wt. %.

7. The use according to claim 1, wherein the mixture further comprises polymers or inorganic or organic fillers.

8. The use according to claim 1, comprising the steps of
(i) mixing BCHPC with the at least one further organic peroxide,
wherein BCHPC is present in solid form, in the form of a solution in an organic solvent or in the form of an aqueous suspension and
the at least one further organic peroxide is present in solid form, in the form of a solution in an organic solvent or in the form of an aqueous suspension,
(ii) optional removal of solvent and/or water and
(iii) optional drying.

9. The use according to claim 1, wherein the at least one organic peroxide in solid form or in the form of an aqueous suspension is mixed with BCHPC in solid form or in the form of an aqueous suspension and water is then optionally removed.

10. The use according to claim 1, wherein the at least one further organic peroxide and the BCHPC are mixed in dry or water-moistened solid form.

11. A composition, comprising BCHPC and at least one substance for reducing the burning rate, wherein the substance for reducing the burning rate is selected from dilauroyl peroxide (LP), dicetyl peroxydicarbonate (CEPC) and dimyristyl peroxydicarbonate (MYPC) and mixtures thereof, and wherein the ratio of BCHPC to the substance for reducing the burning rate is 25:75 wt. % to 75:25 wt. %.

12. The composition according to claim 11, which further comprises at least one desensitising agent, which is an inert solid towards BCHPC, and wherein the proportion of BCHPC relative to the mixture of BCHPC and substance for reducing the burning rate and desensitizing agent is 10 to 90 wt. %.

13. The use of a composition according to claim 11 as initiator in a chemical reaction.

14. The use according to claim 2, wherein the solid form is a powder.

15. The use according to claim 1, wherein the proportion of BCHPC relative to the mixture of BCHPC and further organic peroxide and desensitizing agent is 30 to 60 wt. %.

16. The use according to claim 1, wherein the ratio of BCHPC to further organic peroxide is 40:60 to 60:40 wt. %.

17. The use according to claim 1, wherein the ratio of BCHPC to desensitising agent is 25:75 to 75:25 wt. %.

18. The use according to claim 1, wherein the ratio of BCHPC to desensitising agent is 40:60 to 60:40 wt. %.

19. The composition according to claim 12, wherein the at least one desensitising agent is dicyclohexyl phthalate, fluorene, aluminium trihydroxide, polystyrene or glyceryl tribenzoate.

20. The use of a composition according to claim 13 in a method for curing an unsaturated polyester resin.

* * * * *